United States Patent [19]

Knollmueller

[11] 3,965,136

[45] June 22, 1976

[54] ALKOXYSILANE CLUSTER COMPOUNDS AND THEIR PREPARATION

[75] Inventor: Karl O. Knollmueller, Hamden, Conn.

[73] Assignee: Olin Corporation, New Haven, Conn.

[22] Filed: Sept. 24, 1975

[21] Appl. No.: 616,438

[52] U.S. Cl. .................. 260/448.8 A; 260/448.8 R; 252/78
[51] Int. Cl.² .......................... C07F 7/04; C07F 7/18
[58] Field of Search ........................... 260/448.8 A

[56] References Cited
UNITED STATES PATENTS

| | | | |
|---|---|---|---|
| 2,566,364 | 9/1951 | Pedlow et al. | 260/448.8 A X |
| 2,711,418 | 6/1955 | Kather et al. | 260/448.8 A |
| 2,995,593 | 8/1961 | Kovacich et al. | 260/448.8 A |
| 3,019,191 | 1/1962 | Furby et al. | 260/448.8 A X |

*Primary Examiner*—Paul F. Shaver
*Attorney, Agent, or Firm*—Kenneth P. Glynn

[57] ABSTRACT

Novel alkoxysilane cluster compounds are described having the formula RSi[Osi(OR')$_3$]$_3$ wherein R is hydrogen, an alkyl, alkenyl, aryl or aralkyl group and each R' is independently selected from the same group as R with the proviso that at least a majority of R' radicals are sterically hindered alkyl groups having at least 3 carbon atoms. The preparation of these novel alkoxysilane cluster compounds is also described.

23 Claims, No Drawings

ALKOXYSILANE CLUSTER COMPOUNDS AND THEIR PREPARATION

The present invention is directed to novel oxysilane compounds and their preparation. More particularly, the present invention is directed to novel alkoxysilane cluster compounds, and their preparation, the compounds having the general formula:

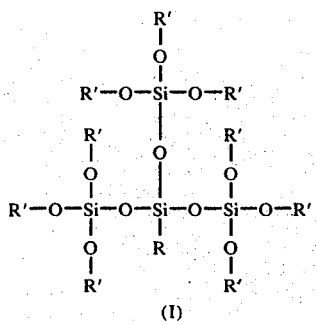

wherein R is hydrogen, an alkyl, alkenyl, aryl or aralkyl and each R' is independently selected from the same group as R with the proviso that at least a majority of R' radicals are sterically hindered alkyl groups having at least 3 carbon atoms. This general Formula (I) may also be written in an abbreviated form as RSi[OSi(OR')$_3$]$_3$ wherein R and R' are as defined.

Silicate esters, silanes and oxysilanes are well known for their utility as functional fluids and many of these compounds have been proproposed for use as heat transfer fluids, hydraulic fluids, brake fluids, transmission fluids, and the like. Novel alkoxysilane compounds with desirable functional fluid properties have now been discovered which have heretofore not been described in the literature. The novel compounds of the present invention are alkoxysilane compounds which are silicon-oxygen balanced cluster compounds of Formula (I) shown above. Morgan et al in the Journal of The American Chemical Society, Vol. 73, pages 5193-5 (1951), describes compounds which are believed to be the closest prior art compounds to those of the present invention, but the Morgan et al compounds are centered with a silicon atom completely enclosed by oxygen atoms, unlike the compounds of the present invention.

As mentioned, the compounds of the present invention are those represented by the Formula (I) above wherein R is hydrogen, an alkyl, alkenyl, aryl or aralkyl. Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In Formula (I), each R' is independently selected from the same group as R, with the proviso that at least a majority of the R' radicals are sterically hindered alkyl groups having at least 3 carbon atoms. The desired and preferred groups for R' are the same as for R subject to the preceding proviso. Desirably, at least a majority of the R' radicals are sterically hindered alkyl groups having about 3 to about 24 carbon atoms and preferably are sterically hindered alkyl groups having about 4 to about 12 carbon atoms. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, and 2,4-dimethyl-3-pentyl, etc.

In the method of preparing the novel alkoxysilane cluster compounds of the present invention a trihalosilane is reacted with a trialkoxysilanol in the presence of a hydrogen halide acceptor base, and optionally a solvent, to obtain a cluster compound containing product.

The trihalosilane used in the method of preparing the cluster compounds of the present invention is a substituted trihalosilane of the formula:

$$R\text{-}SiX_3 \text{ TM} \qquad (II)$$

wherein R is that which is defined above and each X is a halogen selected from F, Cl, Br and I, preferably from Cl, Br and I, especially Cl.

The trihalosilane of Formula (II) above is reacted with a trialkoxysilanol with sterically hindered alkoxy groups which is represented by the formula:

$$HOSi(OR')_3 \text{ TM} \qquad (III)$$

wherein R' is defined above.

The trihalosilane and trialkoxysilanol are reacted in the presence of a hydrogen halide acceptor base compound. The acceptor may be any compound which will accept hydrogen halide and thereby promote the formation of the cluster compounds of the present invention pursuant to Equation (A) shown below. Among the preferred acceptors are the nitrogenated tertiary organic base compounds having at least 3 carbon atoms, e.g., the lower alkyl and aryl tertiary amines such as triethyl amine, tributyl amine, as well as pyridine, substituted pyridine, N,N'-dimethylaniline, etc.

The formation of the novel cluster compounds of the present invention using the above reactants may be represented by the following equation:

$$R\text{—}SiX_3 + 3HOSi(OR')_3 + 3Z \xrightarrow{\text{solvent}} R\text{—}Si[OSi(OR')_3]_3 + 3Z\cdot HX \qquad (A)$$

wherein Z is the hydrogen halide acceptor base and the other reactants are described above.

Equation (A) suggests that the principal reaction in the method of preparing the cluster compounds of the present invention be carried out in a solvent. While the solvent is not necessary, it does serve to moderate the rate of reaction and thereby to enhance the separation of the acceptor Z-hydrogen halide HX from the cluster compound product. The solvent used may be any non-protonic solvent which dissolves the reactants and does not interfere with the Equation (A) reaction. Among the solvents which may be used are benzene, toluene, xylene, high boiling petroleum ether, other ethers such as tetrahydrofurane, and the like.

In general, a stoichiometric excess of the trialkoxysilanol over the trihalosilane is employed to enhance the formation of the cluster compounds of the present invention and to promote completion of the desired reaction. Thus about 2.5 moles to about 10 moles of the trialkoxysilanol is used per mole of trihalosilane and preferably at least about 3 moles to about 6 moles of the trialkoxysilanol is used. The total solvent used in the reaction is a matter of choice and not critical to the reaction, although good results are achieved when about 20 moles to about 80 moles, and preferably about 40 to about 60 moles of solvent is used per mole of trihalosilane. In general, about 0.3 to about 6 parts of solvent per part by weight of total reactants, and preferably about 1 to about 6 parts of solvent per part by weight of total reactants may be used. The hydrogen halide acceptor base is advantageously used in a stoichiometric amount based on the amount of trihalosilane used, e.g., about 3 moles of acceptor per mole of trihalosilane. In general, about 2.5 to about 10 moles, and preferably about 3 to about 6 moles of the acceptor is used per mole of trihalosilane.

The reaction represented by Equation (A) may be performed at very low temperatures, room temperature, or even very high temperatures as long as there is no detrimental effect on the reactants or products. Thus, the reaction may be carried out at $-30°C$ up to the reflux temperature of the lowest boiling constituent, and it is preferably carried out at about 0°C to about 100°C. In a preferred batch method embodiment, the reaction is started at a low temperature, e.g., between $-10°C$ and 20°C, to minimize losses of volatile trihalosilanes and is completed at a higher temperature to drive the reaction as far as possible to completion. Of course, a continuous operation may be employed with a series of reactors in which the first reactor is maintained at the lower temperature and each subsequent reactor is incrimentally higher in temperature to drive the reaction to completion. In any event, the cluster compounds are separated from the product mixture by filtrations, distillations or other conventional separation techniques, and the particular separation system chosen merely depends upon the desired purity of the final product and its ultimate utility.

In addition to the principal reaction of Equation (A) above, some other reactions may occur, one of which is represented by the following equation:

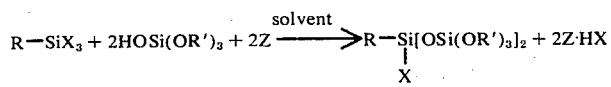

wherein R, R', X and Z are defined above. The product of Equation (B) may simply be separated from the novel cluster compounds of the present invention obtained pursuant to Equation (A) or it may be converted to a cluster compound of the present invention, either in situ or upon separation and recycle, by the addition of excess trialkoxysilanol, according to the following equation:

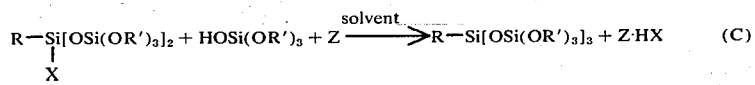

It is preferred to convert as much of the product of Equation (B) into the cluster compounds of the present invention as possible, according to Equation (C) above. However, some amount of an alkoxysilanol will be produced from the product of Equation (B) due to water present which is produced by the condensation of a portion of the trialkoxysilanol starting material, Formula (III) above. This condensation results from the catalytic influence of the acceptor base-hydrogen halide in the reaction mixture, as follows:

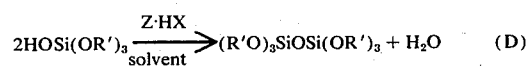

The disiloxane produced is a by-product which may be separated from the cluster compound product by conventional techniques such as fractionation. The water produced according to Equation (D) above is, as mentioned, reactive with the product of Equation (B) to form an alkoxysilanol. This is represented by the following reaction equation:

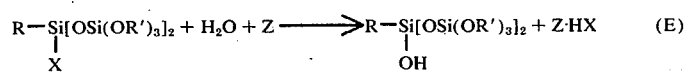

This alkoxysilanol is itself a useful functional fluid, as are other intermediates and by-products shown above. However, it may readily be separated from other product constituents and converted to the desirable cluster compounds of the present invention by reacting it with about 1 to about 20 moles, and preferably about 1 to about 6 moles of a halosilane per mole of alkoxysilanol, the halosilane having the formula:

wherein X and R' are defined above. This reaction includes the use of an acceptor base and may be carried out with similar amounts of base and under the same conditions as set forth above for the reaction of Equation (A). Generally, a temperature of about $-30°C$ to about the reflux temperature of the lowest boiling constituent, preferably about 20°C to about 80°C, may be used. The reaction is represented by the following equation:

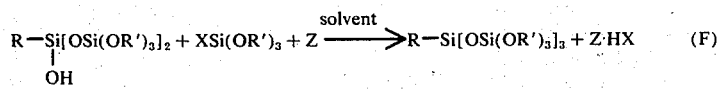

$$R-\underset{\underset{OH}{|}}{Si}[OSi(OR')_3]_2 + XSi(OR')_3 + Z \xrightarrow{\text{solvent}} R-Si[OSi(OR')_3]_3 + Z\cdot HX \qquad (F)$$

The cluster compound product is separated from the other products in the manner discussed above for the reaction of Equation (A).

The novel cluster compounds obtained by the method of the present invention are those represented by Formula (I) above and contain an adequate number of silicon atoms to produce good lubricating properties without the need to add lubricity improvers. Additionally, the silicon atoms are adequately shielded by the significant number of sterically hindered alkyl groups having at least 3 carbon atoms and this assures protection against attack by water. Thus, the novel cluster compounds of the present invention have been found to have good hydrolytic stability, good lubricating properties, and low ASTM viscosity indices with many having pour points below −40°C. The novel cluster compounds exhibit these properties both in substantially pure form and in mixture with the alkoxysilanols obtained by the reaction set forth in Equation (E) above.

The following examples illustrate various embodiments of the present invention, but the present invention should not be construed to be limited thereto:

EXAMPLE 1

A one liter flask is equipped with a heater, stirrer, reflux condenser, thermometer and equilibrated dropping funnel. To prevent moisture from entering, the reflux condenser is topped with a $CaCl_2$ tube while a slow stream of dry nitrogen is passed through the apparatus via the equilibrated dropping funnel. The flask is charged with 57.85 grams (0.219 moles) of a trialkoxysilanol having the formula $HOSi(OC_4H_9 \text{ sec.})_3$, 24 grams (0.303 moles) of pyridine as the acceptor base and 300 ml. of benzene solvent. A solution of 10.9 grams (0.073 moles) of a trihalosilane having the formula $CH_3SiCl_3$ in 90 ml. of benzene is placed into the dropping funnel. The flask contents are set at an initial temperature of 15°C and the trihalosilane solution is added dropwise at such a rate as to maintain the initial temperature of 15°C. After the addition is completed, the contents of the flask are stirred without cooling for about 30 minutes and are then heated to 55° C and maintained at that temperature for about 5 hours. The contents of the flask are then allowed to cool to room temperature and allowed to stand for about 12 hours.

The product mixture obtained is first passed through a filter to remove the pyridine hydrochloride which forms. Next the benzene phase product mixture filtrate is extracted with 200 ml of water so as to hydrolize any Si-Cl bonds to Si-OH bonds. The extraction is performed four times and after the last wash the water is chloride free. The mixture is then passed over $CaCl_2$ and $MgSO_4$ to remove any water remaining therein, and is then subjected to vacuum stripping.

The filtered, hydrolized, dried product (crude weight 58.4 grams) is fed to a micro vigreux stripping column at about 0.05 mm Hg.

The first and second fractions are removed at the 60° to 140°C range and found to contain unreacted trialkoxysilanol and disiloxanes (total weight 11.2 grams).

The third fraction is taken off at about 148 to 150°C and found to be about 9.4 grams of a product having the formula $CH_3Si[OSi(OC_4H_9\text{sec.})_3]_2OH$. The generic formula is $C_{35}H_{58}O_9Si_3$. Based on this formula, the calculated component amounts are determined to be: C—51.24%; H—9.8%; Si—14.38%; found C—52.4%; H—9.74%; Si—14.2%. The —OH radical is confirmed by IR analysis. The theoretical molecular weight is 586, and 590 is found.

The fourth fraction is taken off at about 194 to 196°C and is found to be about 34.5 grams (56.7% yield) of a cluster compound product having the formula $CH_3Si[OSi(OC_4H_9\text{sec.})_3]_3$. The generic formula is $C_{37}H_{84}O_{12}Si_4$; calculated C—53.31%; H—10.16%; Si—13.48%; found C—53.3%; H—10.1%; Si—13.7%. Calculated molecular weight 834; found 830.

EXAMPLE 2

The procedure of Example 1 is repeated except that the following amounts of constituents are used to assure the presence of an excess of the trialkoxysilanol during the reaction:

162.5 grams (0.615 moles) of $HOSi(OC_4H_9\text{sec.})_3$;
53.9 grams (0.68 moles) of pyridine in 500 ml of benzene; 19.7 grams (0.132 moles) of $CH_3SiCl_3$ in 80 ml of benzene;

The reaction is carried out at 0°C instead of 15°C and the completion of the reaction is carried out at 60°C for 18 hours instead of 55°C for 5 hours. The recovery procedure for Example 1 is used and 73 grams of $CH_3Si[OSi(OC_4H_9\text{sec.})_3]_3$ cluster compound is obtained in the high boiling fraction. This represents a yield of 66% as compared to 56.7% obtained in Example 1. The lower fractions of Example 2 are analyzed and found to contain a total of about another 12 grams of the cluster compound, resulting in a total overall yield of 77% for the cluster compound.

EXAMPLE 3

The procedure of Example 1 is repeated with a different trialkoxysilane compound and with different amounts of constituents as follows:

106 grams (0.4 moles) of $HOSi(OC_4H_9\text{sec.})_3$;
53 grams (0.67 moles) of pyridine in 400 ml of benzene;
18.1 grams (0.134 moles) of $HSiCl_3$.

The reaction is carried out at 0°C instead of 15°C and is completed at 50°C for 20 hours instead of 55°C for 5 hours. The recovery procedure of Example 1 is used and 81.8 grams (74.5% yield) of a cluster compound having the formula $HSi[OSi(OC_4H_9\text{sec.})_3]_3$ is obtained from the high boiling fractionation withdrawn at about 182° to 184°C at 0.025 mm Hg. The generic formula is $C_{36}H_{82}O_{12}Si_4$; calculated C—52.77%; H—10.09%; Si—13.71%; found C—52.6%; H—10.07%; Si—13.7%. Calculated molecular weight 819; found 850.

EXAMPLE 4

The procedure of Example 1 is repeated with the following constituents and amounts:

333.2 grams (1.26 moles) of $HOSi(OC_4H_9\text{sec.})_3$;

89.7 grams (1.134 moles) of pyridine in 200 ml of benzene;

41.2 grams (0.252 moles) of $C_2H_5SiCl_3$ in 100 ml of benzene.

The initial reaction is carried out at 4°C followed by heating to 65°C for 12 hours. The recovery procedure of Example 1 is repeated and a mid-range fraction boiling at about 162°C at 0.025 mm Hg is found to contain 109.5 grams (72.3% yield) of a product having the formula $C_2H_5Si[OSi(OC_4H_9sec.)_3]_2OH$. The generic formula is $C_{26}H_{60}O_9Si_3$, calculated C—52.96%; H—10.06%; Si—14.02%; found C—52.58%; H—10.16%; Si—13.56%. Calculated molecular weight 601; found 640.

The high boiling fraction is taken off at 181° to 185°C at 0.03 mm Hg is determined to contain 30.4 grams (14.2% yield) of a cluster compound having the formula $C_2H_5Si[OSi(OC_4H_9sec.)_3]_3$. The generic formula is $C_{38}H_{86}O_{12}Si_4$; calculated C—53.86%; H—10.23%; Si—13.26%; found C—53.33%; H—10.26%; Si—13.50%. Calculated molecular weight 847; found 875.

EXAMPLE 5

The procedure of Example 1 is repeated with the following constituents and amounts:

92.5 grams (0.35 moles) of $HOSi(OC_4H_9sec.)_3$;

38.7 grams (0.49 moles) of pyridine in 400 ml of benzene;

24.67 grams (0.117 moles) of phenyl chlorosilane of the formula $C_6H_5SiCl_3$ in 100 ml of benzene.

The reaction is initially carried out at 10°C and then completed at 55°C for 12 hours. The recovery procedure of Example 1 is used and a fraction of product is removed at about 182°C and 0.01 mm Hg and is determined to contain 51.7 grams (68.3% yield) of a product having the formula $C_6H_5Si[OSi(OC_4H_9sec.)_3]_2OH$. The generic formula is $C_{30}H_{60}O_9Si_3$; calculated C—55.5%; H—9.3%; Si—12.98%; found C—55.48%; H—9.4%; Si—12.9%. Calculated molecular weight 649; found 670.

The distillation residue remaining after the above fraction solidifies and is found to contain 14.35 grams (13.7% yield) of a cluster compound having the formula $C_6H_5Si[OSi(OC_4H_9sec.)_3]_3$. This residue is recrystallized from $CH_3OH$ and has a melting point of about 169°C. The generic formula is $C_{42}H_{86}O_{12}Si_4$; calculated C—56.33%; H—9.68%; Si—12.55%; found C—55.99%; H—9.67%; Si—12.60%. Calculated molecular weight 895; found 895.

EXAMPLE 6

The procedure of Example 1 is repeated except that the following constituents and amounts are used:

104.14 grams (0.394 moles) of $HOSi(OC_4H_9sec.)_3$;

43.6 grams (0.55 moles) of pyridine in 400 ml of benzene;

21.2 grams (0.132 moles) of an alkenyl chlorosilane of the formula $C_2H_3SiCl_3$ in 80 ml of benzene.

The initial reaction is carried out at about 6°C for about ½ hour and then the reaction mixture is heated to 55°C and maintained at that temperature for about 12 hours. The recovery procedure of Example 1 is repeated and a mid-range fraction boiling at about 157°C ±1.5°C at 0.02 mm Hg is found to contain 41.4 grams of a compound having the formula $C_2H_3Si[OSi(OC_4H_9sec.)_3]_2OH$. Calculated values of substituents are—C—52.13%; H—9.76%; and Si—14.07%; found C—51.9%; H—9.79%; and Si—13.6%. A high boiling point fraction is taken off at 197°C ±2° at 0.02 mm Hg. This high boiling fraction contains 13.4 grams of an alkoxysilanol cluster compound of the present invention having the formula $C_2H_3Si[OSi(OC_4H_9sec.)_3]_3$. Calculated C—53.99%; H—10.01%; and Si—13.29%; found C—53.31%; H—10.02%; and Si—13.6%.

EXAMPLE 7

This example demonstrates the conversion of the silanol cluster compound: $RSi[OSi(OR')_3]_2OH$ into a cluster compound of the present invention: $RSi[OSi(OR')_3]_3$.

A 1-liter, three-neck flask equipped as described in Example 1 is charged with 80 grams (0.133 moles) of $C_2H_5Si[OSi(OC_4H_9sec.)_3]_2OH$ (lower boiling component isolated in Example 4); 31.2 grams (0.394 moles) of pyridine and 300 ml of benzene. The mixture is held at 20°C and a solution of 45 grams (0.16 moles) of $(sec.C_4H_9O)_3SiCl$ in 80 ml of benzene is added within 30 minutes. A small exotherm is observed. The reaction mixture is heated for 12 hours to 80°C. The pyridine hydrochloride is removed by filtration and residual SiCl bonds are hydrolyzed by washing with water until the wash is $Cl^-$ free. The organic phase is dried over $MgSO_4$ and the solvent is vacuum stripped. The residue, weighing about 115 grams, is fed into a Vigreux column fractionator and distilled in vacuo. After taking off lower boiling by-products boiling up to 180°C a 0.03 mm Hg the product corresponding to the formula $C_2H_5Si[OSi(OC_4H_9sec.)_3]_3$ is obtained at about 183°C ±5°C at 0.03 mm Hg at a 70% yield. The product is identical with the higher boiling product of Example 4.

The products obtained from the above examples are tested for viscosity, wear scar, hydrolysis solids, weight loss and flash point as shown in the following table. The ASTM slope based on viscosity measurements at 100°F and 210°F are calculated and used as an indication of change in viscosity in response to temperature changes. The wear scar test is performed with a four ball 40 kg load apparatus at 1800 rpm and 168°F for 1 hour. The hydrolysis solids test is carried out at 210°F in the presence of ⅓ weight $H_2O$ and copper metal catalyst for 100 hours. The results establish that the compounds of the present invention are very good functional fluids, as follows:

TABLE

| | Physical Properties | | | | | | | |
|---|---|---|---|---|---|---|---|---|
| | Viscosity (centistokes) | | | ASTM | Wear | % Solids After | Weight Loss In Air 1 hr | Flash |
| Compound tested: | −40°F | 100°F | 210°F | Slope | Scar (mm) | Hydrolysis | 1 atm, 400°F | Point |
| [(sec.$C_4H_9O)_2SiO]_3SiCH_3$ | 1050 | 37.2 | 10 | 0.45 | 0.73 | 0.02 | 13.96% | 390°F |
| [(sec.$C_4H_9O)_3SiO]_3SiH$ | 544.8 | 26.1 | 8.02 | 0.46 | 0.98 | <0.005 | 19.16% | 380°F |
| [(sec.$C_4H_9O)_3SiO]_3SiC_2H_5$ | 1505 | 45.21 | 12.33 | 0.44 | 0.57 | 0.01 | | |

TABLE-continued

| | Physical Properties | | | | | | | |
|---|---|---|---|---|---|---|---|---|
| | Viscosity (centistokes) | | | ASTM | Wear | % Solids After | Weight Loss In Air 1 hr | Flash |
| Compound tested: | −40°F | 100°F | 210°F | Slope | Scar (mm) | Hydrolysis | 1 atm, 400°F | Point |
| [(sec.C$_4$H$_9$O)$_3$SiO]$_3$Si—CH=CH$_2$ | frozen | 42.7 | 11.04 | 0.47 | 0.70 | 0.03 | | |

What is claimed is:

1. A compound of the formula:

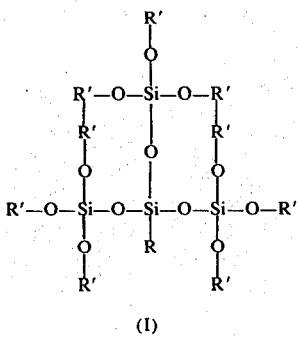

(I)

wherein R is hydrogen, an alkyl, alkenyl, aryl or aralkyl, and each R' is independently selected from the same group as R with the proviso that at least a majority of R' radicals are sterically hindered alkyl groups having at least 3 carbon atoms.

2. The compound of claim 1 wherein R is hydrogen, an alkyl or alkenyl having about 1 to about 18 carbon atoms or an aryl or aralkyl having about 6 to about 24 carbon atoms and wherein each R' is independently selected from the same group as R, subject to the above proviso.

3. The compound of claim 2 wherein a majority of the R' radicals are sterically hindered alkyl groups having about 3 to about 24 carbon atoms.

4. The compound of claim 1 wherein R is hydrogen, an alkyl having about 1 to about 8 carbon atoms or an aryl or aralkyl having about 6 to about 14 carbon atoms and wherein each R' is independently selected from the same group as R, subject to the above proviso.

5. The compound of claim 4 wherein a majority of the R' radicals are sterically hindered alkyl groups having about 4 to about 12 carbon atoms.

6. The compound of claim 1 wherein a majority of the R' radicals are sterically hindered alkyl groups having about 3 to about 24 carbon atoms.

7. The compound of claim 6 wherein a majority of the R' radicals are sterically hindered alkyl groups having about 4 to about 12 carbon atoms.

8. A method of preparing the compound of claim 1 comprising:
reacting a trihalosilane of the formula:

R—SiX$_3$ wherein R is defined in claim 1 above and each X is a halogen selected from F, Cl, Br and I;
with about 2.5 to about 10 moles of a trialkoxysilanol per mole of trihalosilane, said trialkoxysilanol having the formula:

HOSi(OR')$_3$ wherein R' is defined in claim 1 above;
in the presence of about 2.5 to about 10 moles of a hydrogen halide acceptor base compound, per mole of trihalosilane;
said reaction being carried out at about −30°C to about the reflux temperature of the lowest boiling constituent in the reaction mixture.

9. The method of claim 8 wherein X is selected from Cl, Br and I.

10. The method of claim 8 wherein R is hydrogen, an alkyl or alkenyl having about 1 to about 18 carbon atoms or an aryl or aralkyl having about 6 to about 24 carbon atoms and wherein each R' is independently selected from the same group as R with the proviso that at least a majority of the R' radicals are sterically hindered alkyl groups having about 3 to about 24 carbon atoms.

11. The method of claim 10 wherein R is hydrogen, an alkyl having about 1 to about 8 carbon atoms or an aryl or aralkyl having about 6 to about 14 carbon atoms and wherein each R' is independently selected from the same group as R, subject to the above proviso.

12. The method of claim 10 wherein a majority of the R' radicals are sterically hindered alkyl groups having about 4 to about 12 carbon atoms and wherein X is Cl.

13. The method of claim 10 wherein about −3 to about 6 moles of the trialkoxysilanol is used per mole of trihalosilane.

14. The method of claim 13 wherein about 3 to about 6 moles of the hydrogen halide acceptor base compound is used per mole of trihalosilane.

15. The method of claim 14 wherein said reaction is carried out at 0°C to 100°C.

16. A method of preparing the compound of claim 1 comprising:
reacting an alkoxysilanol having the formula:

R—Si[OSi(OR')$_3$]$_2$
   |
   OH wherein R and R' are defined in claim 1 above, with about 1 to about 20 moles of a halosilane per mole of alkoxysilanol, the halosilane having the formula:

XSi(OR')$_3$ wherein R' is defined above and each X is selected from F, Cl, Br and I, in the presence of about 2.5 to about 10 moles of a hydrogen halide acceptor base compound per mole of alkoxysilanol, said reaction being carried out at about −30°C to about the reflux temperature of the lowest boiling constituent in the reaction mixture.

17. The method of claim 16 wherein X is selected from Cl, Br and I.

18. The method of claim 16 wherein R is hydrogen, an alkyl or aralkenyl having about 1 to about 18 carbon atoms or an aryl or aralkyl having about 6 to about 24 carbon atoms and wherein each R' is independently selected from the same group as R with the proviso that at least a majority of the R' radicals are sterically hindered alkyl groups having about 3 to about 24 carbon atoms.

19. The method of claim 18 wherein R is hydrogen, an alkyl having about 1 to about 8 carbon atoms or an aryl or aralkyl having about 6 to about 12 carbon atoms and wherein each R' is independently selected from the same group as R, subject to the above proviso.

20. The method of claim 18 wherein a majority of the R' radicals are sterically hindered alkyl groups having about 4 to about 12 carbon atoms.

21. The method of claim 18 wherein about 1 to about 6 moles of the halosilane is used per mole of alkoxysilanol.

22. The method of claim 21 wherein about 3 to about 6 moles of the hydrogen halide acceptor base compound is used per mole of trialkoxyhalosilane.

23. The method of claim 22 wherein said reaction is carried out at 0°C to 100°C.

* * * * *

PO-1050
(5/69)

UNITED STATES PATENT OFFICE
CERTIFICATE OF CORRECTION

Patent No. 3,965,136                    Dated June 22, 1976

Inventor(s) Karl O. Knollmueller

It is certified that error appears in the above-identified patent and that said Letters Patent are hereby corrected as shown below:

Column 2, line 25, Formula (II) should read --$R-SiX_3$--.

Column 2, line 33, Formula (III) should read --$HOSi(OR')_3$--.

Column 4, line 51, Formula (IV) should read --$XSi(OR')_3$--.

Column 9, claim 1, Formula (I) should read

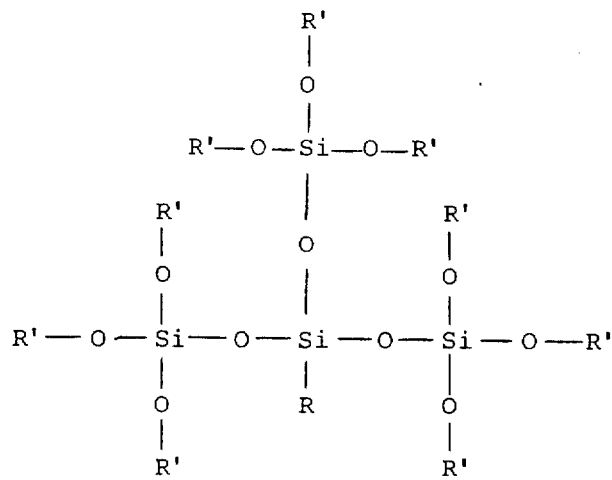

(I)

Column 10, line 31, claim 13, "—3" should read --3--.

Signed and Sealed this

First Day of February 1977

[SEAL]

Attest:

RUTH C. MASON
Attesting Officer

C. MARSHALL DANN
Commissioner of Patents and Trademarks